(12) United States Patent
Ellington et al.

(10) Patent No.: US 9,421,154 B2
(45) Date of Patent: Aug. 23, 2016

(54) COMPOSITION AND PROCESS FOR RELAXING OR STRAIGHTENING HAIR

(75) Inventors: Angela Ellington, Flossmoor, IL (US); Eric Osei-Acquah, Lynwood, IL (US); James Cooper, Chicago, IL (US); Darius Danielski, Chicago, IL (US)

(73) Assignee: L'OREAL, Paris (FR)

( * ) Notice: Subject to any disclaimer, the term of this patent is extended or adjusted under 35 U.S.C. 154(b) by 621 days.

(21) Appl. No.: 12/637,996

(22) Filed: Dec. 15, 2009

(65) Prior Publication Data

US 2010/0158845 A1 Jun. 24, 2010

Related U.S. Application Data

(60) Provisional application No. 61/138,722, filed on Dec. 18, 2008.

(51) Int. Cl.
| | | |
|---|---|---|
| *A61K 8/19* | (2006.01) |
| *A61K 8/34* | (2006.01) |
| *A61K 8/43* | (2006.01) |
| *A61K 8/55* | (2006.01) |
| *A61K 8/58* | (2006.01) |
| *A61K 8/81* | (2006.01) |
| *A61Q 5/04* | (2006.01) |

(52) U.S. Cl.
CPC . *A61K 8/19* (2013.01); *A61K 8/345* (2013.01); *A61Q 5/04* (2013.01)

(58) Field of Classification Search
CPC ......... A61K 8/19; A61K 8/345; A61K 8/066; A61Q 5/04
See application file for complete search history.

(56) References Cited

U.S. PATENT DOCUMENTS

| | | | |
|---|---|---|---|
| 3,433,868 A | 3/1969 | Brechner et al. | |
| 3,654,936 A | 4/1972 | Wajaroff | |
| 4,767,617 A | 8/1988 | Shansky et al. | |
| 5,171,565 A * | 12/1992 | Akhtar et al. | 424/70.4 |
| 5,304,370 A * | 4/1994 | Hawkins et al. | A61K 8/066 132/205 |
| 6,010,690 A * | 1/2000 | Varco | 424/70.13 |
| 6,709,648 B2 * | 3/2004 | Sako et al. | 424/70.12 |

FOREIGN PATENT DOCUMENTS

| | | |
|---|---|---|
| CA | 2408104 A1 * | 11/2011 |
| DE | 195 36 423 | 4/1996 |
| DE | 197 14 162 | 8/1998 |
| EP | 0 363 057 | 4/1990 |
| EP | 1 449 512 | 8/2004 |
| JP | 5 306212 A | 11/1993 |

OTHER PUBLICATIONS

Extended European Search Report dated Jul. 14, 2010 in corresponding European Patent Application No. 09 306 260.2.
Database WPI Week 199351, Thomson Scientific, London, GB, 1993-408827, XP00258827 & JP 5 306212 A (KAO CORP) Nov. 19, 1993 abstract.
T.J. Elliott, "Use of a Laboratory model to Evaluate the factors Influencing the Performance of Depilatories," Journal of the Society of Cosmetic Chemist, 25, pp. 367-377, 1974 Society of Cosmetic Chemists of Great Britain.
William C. Griffin, "Calculation of HLB values of non-ionic surfactants", Journal of the Society of Cosmetic Chemists, vol. 5, pp. 249-256, 1954, Society of Cosmetic Chemists of Great Britain.

* cited by examiner

*Primary Examiner* — Mina Haghighatian
*Assistant Examiner* — Helen Chui
(74) *Attorney, Agent, or Firm* — Maria Luisa Balasta; Runzhi Zhao

(57) ABSTRACT

The present invention is directed to composition for straightening or relaxing hair containing: (a) at least one hydroxide-containing active ingredient; (b) at least one polyhydric alcohol having 4 or more carbon atoms and two hydroxyl groups; (c) optionally, at least one nonionic surfactant having an HLB of from about 8 to about 20; (d) optionally, at least one amphoteric and/or zwitterionic surfactant; and (e) remainder, to 100%, of a cosmetically suitable medium.

26 Claims, No Drawings

COMPOSITION AND PROCESS FOR RELAXING OR STRAIGHTENING HAIR

CROSS-REFERENCE TO RELATED APPLICATION

This application claims the benefit of the filing date of U.S. Provisional Application No. 61/138,722, filed Dec. 18, 2008, the contents of which are incorporated by reference.

BACKGROUND OF THE INVENTION

Hair straightening or hair relaxing products have been commercially available for over fifty years for people who want straighter, more manageable hair. Most commercially available hair relaxers are composed of a strong hydroxide base that permanently alters hair shape by chemically targeting keratin's cross-linked bonds Commercial products based only on alkaline metal hydroxides such as sodium hydroxide and lithium hydroxide are typically used to straighten or relax curly/kinky hair. There are primarily four different types of alkaline hydroxide hair straighteners in use: guanidine hydroxide, lithium hydroxide, sodium hydroxide, and potassium hydroxide. The straightening generally occurs within 20-25 minutes. Because all are strong-base relaxers capable of degrading hair keratin, all can over process the hair causing irreversible damage to the fibrous keratin structure leading to hair breakage.

This present invention reduces the total alkalinity thus reducing the chance of degradation of hair keratin as well as over processing the hair, thus decreasing the chance of hair breakage and loss.

BRIEF SUMMARY OF THE INVENTION

The present invention is directed to a composition for straightening or relaxing hair containing:
(a) at least one hydroxide-containing active ingredient;
(b) at least one polyhydric alcohol having 4 or more carbon atoms and two hydroxyl groups;
(c) optionally, at least one nonionic surfactant having an HLB of from about 8 to about 20;
(d) optionally, at least one amphoteric and/or zwitterionic surfactant; and
(e) remainder, to 100%, of a cosmetically suitable medium.

The present invention is also directed to a process for straightening or relaxing hair involving the steps of:
(a) providing a hair straightening or relaxing composition containing:
  i. at least one hydroxide-containing active ingredient;
  ii. at least one polyhydric alcohol having 4 or more carbon atoms and two hydroxyl groups; and
  iii. optionally, at least one non-ionic surfactant having an HLB of from about 8 to about 20;
  iv. optionally, at least one amphoteric and/or zwitterionic surfactant; and
  v. remainder, to 100%, of a cosmetically suitable medium;
(b) applying the composition onto the hair;
(c) physically smoothing the hair to form treated hair;
(d) rinsing the treated hair; and
(e) applying a neutralizer onto the treated hair in order to neutralize any residual hydroxide-containing active ingredient present on the treated hair.

DETAILED DESCRIPTION OF THE INVENTION

Other than in the operating examples, or where otherwise indicated, all numbers expressing quantities of ingredients and/or reaction conditions, are to be understood as being modified in all instances by the term "about".

It has been surprisingly found that by employing a polyhydric alcohol having 4 or more carbon atoms and 2 hydroxyl groups, a lower concentration of hydroxide compound may be used in order to straighten or relax hair which is consequently less damaging to the hair and less harsh to the scalp. Conventional products, which employ higher concentrations of hydroxide, have a tendency to cause both skin irritation, as well as damage to the hair. However, by employing a lower concentration of hydroxide-containing active ingredient, in combination with a polyhydric alcohol having 4 or more carbon atoms and 2 hydroxyl groups, straightening or relaxing of hair can be achieved in a manner that is comparable to conventional products having higher concentrations of hydroxide-containing active ingredients. In addition, the lower concentration of hydroxide active reduces the chances of hair keratin degradation and subsequent decrease in hair strength and/or integrity, thus being safer for both skin and hair.

Hydroxide-Containing Active Ingredient

Suitable hydroxide-containing active ingredients for use in the present invention may be chosen, for example, from alkali metal hydroxides, alkaline-earth metal hydroxides, transition metal hydroxides, and organic hydroxides, such as sodium hydroxide, potassium hydroxide, lithium hydroxide, rubidium hydroxide, caesium hydroxide, francium hydroxide, beryllium hydroxide, magnesium hydroxide, calcium hydroxide, strontium hydroxide, barium hydroxide, molybdenum hydroxide, manganese hydroxide, zinc hydroxide, cobalt hydroxide, cadmium hydroxide, cerium hydroxide, lanthanum hydroxide, actinium hydroxide, thorium hydroxide, aluminium hydroxide, guanidinium hydroxide and quaternary ammonium hydroxides.

A particularly preferred hydroxide-containing active ingredient for use in the present invention is sodium hydroxide.

Whereas conventional hair straightening or relaxing products typically contain anywhere from 2.0 to 2.4% by weight, based on the weight of the product, of a hydroxide-containing active ingredient, depending on the degree of curliness/kinkiness of the untreated hair and/or degree of straightening or relaxing that is desired, less active ingredient is required using the present invention due to the presence of a polyhydric alcohol having 4 or more carbon atoms and 2 hydroxyl groups.

Thus, according to the present invention, the hydroxide-containing active ingredient is typically employed in the hair straightening or relaxing composition in an amount of from about 1.2 to about 1.9% by weight, such as from about 1.4 to about 1.8% by weight, and from about 1.5 to about 1.8 by weight, based on the total weight of the composition.

Polyhydric Alcohol

Suitable examples of polyhydric alcohols having 4 or more carbon atoms and 2 hydroxyl groups include, but are not limited to, butylene glycol, pentylene glycol, hexylene glycol, 1,2-octanediol, 1,2-hexanediol, and the like.

The polyhydric alcohol of the present invention will typically be employed in an amount of from about 0.5 to about 20% by weight, such as from about 1 to about 10% by weight, and from about 1.5 to about 5% by weight, based on the weight of the composition.

Cosmetically Suitable Medium

As used herein, the term "cosmetically suitable medium" is known to one of ordinary skill in the art. A particularly preferred, and conventionally used, medium is water.

The composition may be employed in any suitable form such as a cream emulsion, lotion, gel, mousse and the like.

Acidic Neutralizing Composition

After application of the hair straightening or relaxing composition of the present invention, it is necessary to neutralize and remove any residual hydroxide-containing active ingredients present on the hair and scalp in order to further lessen any damage and irritation that may potentially occur. For optimum results, the neutralizing composition, preferably in the form of a rinse-off shampoo, should have an acidic pH in the range of from about 2 to 5, preferably about 2.5 to 4.5. The acidic neutralizing composition can contain organic and/or inorganic acids. Examples thereof include, but are not limited to, salicylic acid, citric acid, HCl, malic acid, succinic acid, glutamic acid, sorbic acid, benzoic acid, tartaric acid, lactic acid, acetic acid, glycolic acid and fumaric acid.

The hair straightening/relaxing composition disclosed herein may be, for example, in the form of a thickened cream. These creams are made in the form of "heavy" emulsions, for example, based on glyceryl stearate, glycol stearate, self-emulsifying waxes, fatty alcohols, mineral oil and petrolatum.

Liquids or gels containing thickeners, such as carboxyvinyl polymers or copolymers that "stick" the hairs together and hold them in a smooth position during the leave-in time, may also be used.

The hair straightening/relaxing composition as disclosed herein may also comprise at least one adjuvant chosen, for example, from silicones in soluble, dispersed and microdispersed forms, nonionic, anionic, cationic and amphoteric surfactants, ceramides, glycoceramides and pseudoceramides, vitamins and provitamins including panthenol, waxes other than ceramides, glycoceramides and pseudoceramides, water-soluble and liposoluble, silicone-based and non-silicone-based sunscreens, nacreous agents and opacifiers, sequestering agents, plasticizers, solubilizers, acidifying agents, mineral and organic thickeners, antioxidants, hydroxy acids, penetrating agents, fragrances, and preserving agents.

According to a preferred embodiment, the straightening/relaxing composition of the present invention further comprises at least one nonionic surfactant having an HLB of from 8 to 20.

The term "HLB" is well known in the art, and denotes the Hydrophilic Lipohilic Balance of a surfactant.

In the present invention, the HLB of the surfactants is the HLB as defined by GRIFFIN in the publication J. Soc. Cosm. Chem. 1954 (Volume 5), pages 249-256.

Suitable nonionic surfactants include those containing a hydrophobic moiety such as a long chain alkyl group or alkylated aryl group containing from 8 to 30 carbon atoms and a hydrophilic chain comprising one or more ethoxy moieties or a combination of one or more ethoxy moieties and one or more propoxy moieties, where the total number of moles of ethoxy and propoxy moieties is greater than or equal to 10.

Preferred nonionic surfactants for use in the present invention are chosen from (poly)ethoxylated esters of sorbitan and of fatty acids, containing up to 150 moles of ethylene oxide. Suitable fatty acids contain from 8 to 30 carbon atoms.

The nonionic surfactant may be present in the composition of the present invention in an amount of from about 0.0 to about 15.0% by weight, such as from about 0.25 to about 12.0% by weight, and from about 0.5 to about 10.0% by weight, based on the weight of the composition.

According to preferred embodiment, the straightening/relaxing composition of the present invention further comprises at least one amphoteric and/or zwitterionic surfactant.

Suitable amphoteric and/or zwitterionic surfactants which may be employed include, but are not limited to, alkyl amine oxides, alkyl betaines, alkyl amidopropyl betaines, alkyl sulphobetaines (sultaines), alkyl glycinates, alkyl carboxyglycinates, alkyl amphopropionates, alkyl amphoglycinates, alkyl amidopropyl hydroxysultaines, acyl taurates and acyl glutameates, wherein the alkyl and acyl groups have from about 8 to about 19 carbon atoms.

The amphoteric and/or zwitterionic surfactant may be present in the composition of the present invention in an amount of from about 0.0 to about 10.0% by weight, such as from about 0.0 to about 0.5% by weight, and from about 0.0 to about 3.0% by weight, based on the weight of the composition.

According to another embodiment of the present invention, there is provided a process for straightening or relaxing hair involving the steps of:

(a) contacting the hair with the above-disclosed hair straightening or relaxing composition for a period of time less than about 30 minutes, such as less than about 20 minutes;
(b) physically smoothing the hair in order to form treated hair;
(c) rinsing the treated hair in order to remove any excess hair straightening or relaxing composition from the treated hair; and
(d) applying a neutralizing composition containing at least one acidic neutralizing ingredient onto the treated hair in order to neutralize any residual hydroxide-containing active ingredient present on the hair and scalp, the neutralizing composition preferably being in the form of a shampoo.

Physically smoothing the hair can be performed by any suitable apparatus such as, for example, a hair brush or comb.

In commercially available hair straightening or relaxing compositions, higher concentrations of hydroxide-containing compounds must be used in order to satisfactorily straighten or relax the hair. In the present invention, however, because of the synergy realized with the use of a polyhydric alcohol having 4 or more carbon atoms and 2 hydroxyl groups, lower concentrations of hydroxide-containing compounds can be used. Alternatively, when the same or similar concentration of hydroxide-containing compounds is used as in prior art compositions, a more efficient/faster straightening or relaxing result is achieved.

Therefore, the present invention also concerns the use of a polyhydric alcohol having 4 or more carbon atoms and hydroxyl groups for improving the hair straightening or relaxing effect of hydroxide-containing compounds.

According to a preferred embodiment, said polyhydric alcohol is hexylene glycol.

According to another preferred embodiment, said hydroxide-containing compound is sodium hydroxide.

Moreover, due to the lower concentrations of hydroxide-containing compounds being used, a barrier substance is typically not required when using the hair straightening/relaxing composition of the present invention. Commercially available hair relaxing products oftentimes require the hair stylist to apply a barrier substance such as petrolatum to the skin surrounding the scalp and the area around the ears. The barrier substance is used to prevent the skin from becoming irritated if the hair relaxing product contacts the skin. A barrier substance is not necessary when using the process of the present invention because the concentration of hydroxide compound is much lower.

The present invention will be better understood from the examples which follow, all of which are intended for illustrative purposes only, and are not meant to unduly limit the scope of the invention in any way.

Examples

The following hair straightening/relaxing compositions were prepared (in the tables hereunder, the amounts are expressed in percentages by weight, with regard to the total weight of the composition).

COMPARATIVE FORMULA 1

| Ingredients (INCI names) | Trade Name | Manufacturer | % by weight |
|---|---|---|---|
| Petrolatum | | | 23 |
| Mineral oil | | | 13.5 |
| Cetearyl alcohol and Polysorbate 60 (1) | Polawax NF | Croda | 10.0 |
| PEG-75 lanolin (2) | Super Solan Flakes | Croda | 0.75 |
| Laneth-15 (3) | Polychol 15 | Croda | 0.75 |
| Propylene glycol | | | 3.0 |
| Sodium hydroxide as a 50% by weight solution in water please confirm | | | 4.70 (2.35% NaOH) |
| PG-Hydroxyethylcellulose Cocodimonium chloride (4) | Crodacel QM | Croda | 0.05 |
| Hydrolysed wheat protein and hydrolysed wheat starch (5) | Cropeptide W | Croda | 0.05 |
| Water | | | 44.20 |

INVENTIVE FORMULA 2

| Ingredients (INCI names) | % by weight |
|---|---|
| Petrolatum | 23 |
| Mineral oil | 13.5 |
| Cetearyl alcohol and Polysorbate 60 (1) | 10.0 |
| PEG-75 lanolin (2) | 0.75 |
| Laneth-15 (3) | 0.75 |
| Hexylene glycol | 3.0 |
| Sodium hydroxide as a 50% by weight solution in water please confirm | 3.5 (1.75% NaOH) |
| PG-Hydroxyethylcellulose Cocodimonium chloride (4) | 0.05 |
| Hydrolysed wheat protein and hydrolysed wheat starch (5) | 0.05 |
| Water | 45.4 |

INVENTIVE FORMULA 3

| Ingredients (INCI names) | % by weight |
|---|---|
| Petrolatum | 23 |
| Mineral oil | 13.5 |
| Cetearyl alcohol and Polysorbate 60 (1) | 10.0 |
| PEG-75 lanolin (2) | 0.75 |
| Laneth-15 (3) | 0.75 |
| Propylene glycol | 1.5 |
| Hexylene glycol | 1.5 |
| Sodium hydroxide as a 50% by weight solution in water please confirm | 3.8 (1.9% NaOH) |
| PG-Hydroxyethylcellulose Cocodimonium chloride (4) | 0.05 |
| Hydrolysed wheat protein and hydrolysed wheat starch (5) | 0.05 |
| Water | 45.10 |

Two criteria that are important for new relaxers are that the formulas must have comparable straightening and have improved hair integrity when compared to prior art relaxers.

General Procedure to Test the Straightening Efficiency of Kinky Hair:

A sample of virgin African-American curl classification VI hair (sample lot number 050509-10) was used for all treatments and thermal, chemical, and mechanical tests. The sample was of excellent quality as determined by amino acid analysis (Cy A=0.4; Lan=0.0; and Tyr=2.1). The standard swatches were prepared to have a final weight of 250 mg and length after extension of 7 cm.

The following treatments were performed:
Hair swatches were treated with the appropriate relaxer formula in a 1:4 hair-to-relaxer weight ratio. The relaxer formulas were left on the hair swatches for 15 minutes and were rinsed off with water calibrated to 40° C.

Following the treatment defined above, the straightened hair swatches were shampooed using an aqueous solution of 10% by weight of Ammonium Lauryl Sulfate, then rinsed two times with water. The swatches were then blotted dry.

The hair treated with the relaxer formulas containing hexylene glycol, as shown in Table 1 below, had comparable straightening when compared to the hair treated with the comparative formula (Formula 1).

In order to evaluate the integrity of hair treated with the new formulas, differential scanning calorimetry (DSC) is used to determine the internal properties of hair proteins. In general, the DSC instrumentation evaluates the properties of hair proteins using two different data points: (1) the denaturation temperature ($T_d$) and (2) the change in enthalpy during denaturation ($\Delta H_d$) of hair proteins. The $T_d$ values are correlated to the density of the hair protein, while the $\Delta H_d$ values are related to the energy required to break the bonds of the proteins. To consider integrity to be improved after a relaxer process, the $T_d$ and $\Delta H_d$ values must be greater than those for a currently marketed relaxer Formula 1 ($T_d$=138.29° C. and $\Delta H_d$=8.13 J/g).

When hair was treated with 1.75% by weight NaOH and 3% by weight hexylene glycol (Formula 2), both the $T_d$ and $\Delta H_d$ values trended toward higher values than Formula 1, indicating the integrity of the hair was better maintained compared to the commercial product.

For the formula containing a mixture of glycols (Formula 3), the $T_d$ and $\Delta H_d$ values were also better than the benchmark formula. Overall, the DSC results demonstrate that hexylene glycols in relaxers maintains the integrity of hair better than Formula 1 with comparable straightening at reduced hydroxide concentrations.

TABLE 1

Thermal DSC data for virgin hair and hair treated with the three test formulas:

| | Denaturation temperature ($T_d$) (° C.) | Total enthalpy ($\Delta H_d$) (J/g) |
|---|---|---|
| Formula 1 | 138.29 ± 3.90 | 8.13 ± 1.04 |
| Formula 2 | 144.70 ± 0.24 | 11.10 ± 0.43 |
| Formula 3 | 145.08 ± 1.14 | 10.46 ± 1.56 |
| Virgin Hair (control) | 152.01 ± 0.32 | 19.57 ± 1.72 |

In order to evaluate the straightening efficacy of the relaxing process, an intermittent modulus device (TMD) was used to compare the benchmark to the test formulas containing hexylene glycol. The intermittent modulus technique mimics the chemical straightening procedure by measuring the stress-strain modulus of hair in terms of hair elongation and axial swelling. A description of a laboratory model of an analogous device used in the study can be found in Elliot, "Use of a Laboratory model to Evaluate the factors Influencing the Performance of Depilatories," J. Soc. Cosm. Chem., 25, 367 (1974).

This instrumentation uses a single strand of hair immersed in relaxer cream. A constant load is placed on the hair fiber and an additional load is applied at intermittent intervals. Changes in the length of the fiber in time are recorded, and used to determine: (1) the supercontraction time and (2) the elongation rate. In general, the supercontraction time is equated to the breakdown of curl, while the elongation rate is the speed at which fiber extends under specified conditions. Ideally, newly developed formulas should have supercontraction times and elongation rate not substantially higher than the ones obtained with the prior art formula.

As a basis of comparison, Formula 1 yielded supercontraction times of about 13.8 mins and extension rates of about 0.47 mm/min. The inventive Formulas 2 and 3 showed a shorter supercontraction time of 12.9 and 13.3 min, respectively, indicating faster breakdown of hair.

Similarly, the elongation rates of the inventive Formulas 2 and 3 were either closely similar (0.45 mm/min for Formula 2) or slightly higher (0.54 mm/min for Formula 3) than the comparative formula. This data indicates that these reduced active formulas containing hexylene glycol yield chemical straightening that are comparable to the comparative formula containing a substantially higher amount of NaOH.

The results obtained are presented in Table 2 hereunder:

TABLE 2

| | IMD results | | |
|---|---|---|---|
| | Average supercontraction | Average elongation rate (mm/min) | |
| Formula | (min) | Pulse load | Constant load |
| Formula 1 | 13.8 | 0.47 | 0.24 |
| Formula 2 | 12.9 | 0.45 | 0.25 |
| Formula 3 | 13.3 | 0.54 | 0.29 |

As can be seen from the above data, the use of a polyhydric alcohol having 4 or more carbon atoms and 2 hydroxyl groups, in combination with a hydroxide-containing compound, yields a synergy in hair straightening or relaxing which, in turn, facilitates the use of less hydroxide-containing compound to achieve good results, in a manner which causes less damage to hair fibers and irritation to the skin.

What is claimed is:

1. A composition for straightening or relaxing hair comprising:
   (a) a hydroxide-containing active ingredient selected from the group consisting of lithium hydroxide, sodium hydroxide, and potassium hydroxide, wherein (a) is present in an amount of from about 1.2 to about 1.9% by weight, based on the weight of the composition;
   (b) a mixture of hexylene glycol and butylene glycol, which is present in an amount of about 3% to about 20% by weight, based on the weight of the composition;
   (c) optionally, at least one nonionic surfactant having an HLB of from about 8 to about 20;
   (d) optionally, at least one amphoteric and/or zwitterionic surfactant; and
   (e) remainder, to 100% by weight based on the weight of the composition, a cosmetically suitable medium.

2. The composition of claim 1, wherein (a) the hydroxide-containing active ingredient is sodium hydroxide.

3. The composition of claim 2, wherein the sodium hydroxide is present in an amount of about 1.5% by weight, and the mixture of hexylene glycol and butylene glycol is present in an amount of about 3.0% by weight, based on the weight of the composition.

4. The composition of claim 1, wherein (a) the hydroxide-containing active ingredient is lithium hydroxide.

5. The composition of claim 4, wherein the lithium hydroxide is present in an amount of about 1.5% by weight, and the mixture of hexylene glycol and butylene glycol is present in an amount of about 3.0% by weight, based on the weight of the composition.

6. The composition of claim 1, wherein (a) is present in an amount of from about 1.5 to about 1.8% by weight, based on the weight of the composition.

7. The composition of claim 1, wherein (b) is present in an amount of about 20% by weight, based on the weight of the composition.

8. The composition of claim 1, wherein (b) is present in an amount of about 3% by weight, based on the weight of the composition.

9. The composition of claim 1 comprising (c) at least one nonionic surfactant, wherein the at least one nonionic surfactant is selected from the group consisting of (poly)ethoxylated esters of sorbitan having up to 20 moles of ethylene oxide and (poly)ethoxylated esters of fatty acids having up to 20 moles of ethylene oxide.

10. The composition of claim 1, wherein (c) the at least one nonionic surfactant is present in an amount up to about 15.0% by weight, based on the weight of the composition.

11. The composition of claim 1 comprising (d) at least one amphoteric and/or zwitterionic surfactant, wherein the at least one amphoteric and/or zwitterionic surfactant is selected from the group consisting of alkyl amine oxides, alkyl betaines, alkyl amidopropyl betaines, alkyl sulphobetaines, alkyl glycinates, alkyl carboxyglycinates, alkyl amphopropionates, alkyl amphoglycinates, alkyl amidopropyl hydroxysultaines, acyl taurates and acyl glutamates, wherein the alkyl and acyl groups have 8 to 19 carbon atoms.

12. The composition of claim 1, wherein (d) is present in an amount up to about 3.0% by weight, based on the weight of the composition.

13. A process for straightening or relaxing hair comprising:
   (a) providing a hair straightening or relaxing composition containing:
      (i) a hydroxide-containing active ingredient selected from the group consisting of lithium hydroxide, sodium hydroxide, and potassium hydroxide, wherein (i) is present in an amount of from about 1.2 to about 1.9% by weight, based on the weight of the composition;
      (ii) a mixture of hexylene glycol and butylene glycol, which is present in an amount of about 3% to about 20% by weight, based on the weight of the composition;
      (iii) optionally, at least one nonionic surfactant having an HLB of from about 8 to about 20;
      (iv) optionally, at least one amphoteric and/or zwitterionic surfactant; and
      (v) remainder, to 100% by weight based on the weight of the composition, a cosmetically suitable medium;
   (b) applying the composition onto the hair;
   (c) physically smoothing the hair to form treated hair;
   (d) rinsing the treated hair to remove excess composition; and
   (e) applying a neutralizing composition containing at least one acidic neutralizing ingredient onto the treated hair in order to neutralize residual of the hydroxide-containing active ingredient present on the treated hair.

14. The process of claim 13, wherein (a)(i) the hydroxide-containing active ingredient is sodium hydroxide.

15. The process of claim 14, wherein the sodium hydroxide is present in an amount of about 1.5% by weight, and the mixture of hexylene glycol and butylene glycol is present in an amount of about 3.0% by weight, based on the weight of the composition.

16. The process of claim 13, wherein (a)(i) the hydroxide-containing active ingredient is lithium hydroxide.

17. The process of claim 16, wherein the lithium hydroxide is present in an amount of about 1.5% by weight, and the mixture of hexylene glycol and butylene glycol is present in an amount of about 3.0% by weight, based on the weight of the composition.

18. The process of claim 13, wherein (a)(i) is present in an amount of from about 1.5 to about 1.8% by weight, based on the weight of the composition.

19. The process of claim 13, wherein (a)(ii) is present in an amount of about 20% by weight, based on the weight of the composition.

20. The process of claim 13, wherein (a)(ii) is present in an amount of about 3% by weight, based on the weight of the composition.

21. The process of claim 13, wherein the composition comprises (a)(iii) the at least one nonionic surfactant, and the at least one nonionic surfactant is selected from the group consisting of (poly)ethoxylated esters of sorbitan having up to 20 moles of ethylene oxide and (poly)ethoxylated esters of fatty acids having up to 20 moles of ethylene oxide.

22. The process of claim 13, wherein (a)(iii) the at least one nonionic surfactant is present in an amount up to about 15.0% by weight, based on the weight of the composition.

23. The process of claim 13, wherein the composition comprises (a)(iv) the at least one amphoteric and/or zwitterionic surfactant and the at least one amphoteric and/or zwitterionic surfactant is selected from the group consisting of alkyl amine oxides, alkyl betaines, alkyl amidopropyl betaines, alkyl sulphobetaines, alkyl glycinates, alkyl carboxyglycinates, alkyl amphopropionates, alkyl amphoglycinates, alkyl amidopropyl hydroxysultaines, acyl taurates and acyl glutamates, wherein the alkyl and acyl groups have 8 to 19 carbon atoms.

24. The process of claim 13, wherein (a)(iv) is present in an amount up to about 3.0% by weight, based on the weight of the composition.

25. The process of claim 13, wherein the hair straightening or relaxing composition is allowed to remain on the hair for a period of less than 30 minutes.

26. The process of claim 13, wherein the hair straightening or relaxing composition is allowed to remain on the hair for a period of less than 20 minutes.

* * * * *